United States Patent
Hughes et al.

(10) Patent No.: US 6,902,701 B1
(45) Date of Patent: Jun. 7, 2005

(54) APPARATUS FOR SENSING VOLATILE ORGANIC CHEMICALS IN FLUIDS

(75) Inventors: Robert C. Hughes, Albuquerque, NM (US); Ronald P. Manginell, Albuquerque, NM (US); Mark W. Jenkins, Albuquerque, NM (US); Richard Kottenstette, Albuquerque, NM (US); Sanjay V. Patel, San Diego, CA (US)

(73) Assignee: Sandia Corporation, Albuquerque, NM (US)

( * ) Notice: Subject to any disclaimer, the term of this patent is extended or adjusted under 35 U.S.C. 154(b) by 177 days.

(21) Appl. No.: 09/974,327

(22) Filed: Oct. 9, 2001

(51) Int. Cl.[7] .................. G01N 21/00; G01N 27/00; G01N 31/00; G01N 33/00; G01N 7/00
(52) U.S. Cl. .................. 422/83; 422/50; 422/56; 422/82.01; 422/82.02; 422/57; 422/61; 422/68.1; 422/69; 422/88; 422/98; 436/43; 436/174; 436/178; 73/1.01; 73/1.02; 73/23.2; 73/53.01; 29/592; 29/592.1
(58) Field of Search .................. 422/50, 56, 82.01, 422/82.02, 57, 61, 68.1, 69, 83, 88, 98; 73/1.01, 1.02, 23.2, 53.01; 436/43, 174, 178; 29/592, 592.1

(56) References Cited

U.S. PATENT DOCUMENTS

| | | | |
|---|---|---|---|
| 3,045,198 A | | 7/1962 | Dolan .................. 338/13 |
| 4,129,030 A | | 12/1978 | Dolan .................. 73/34.05 |
| 4,224,595 A | | 9/1980 | Dolan .................. 338/34 |
| 4,237,721 A | | 12/1980 | Dolan .................. 73/31.05 |
| 4,759,210 A | * | 7/1988 | Wohltjen .................. 73/31.07 |
| 4,818,348 A | * | 4/1989 | Stetter .................. 205/780 |
| 5,224,972 A | | 7/1993 | Frye .................. 55/18 |
| 5,469,369 A | * | 11/1995 | Rose-Pehrsson et al. ..... 702/27 |
| 5,501,893 A | | 3/1996 | Laermer .................. 428/161 |
| 5,545,300 A | * | 8/1996 | Yun et al. .................. 204/424 |
| 5,571,401 A | * | 11/1996 | Lewis et al. .................. 205/787 |
| 5,951,846 A | | 9/1999 | Lewis .................. 205/787 |
| 6,085,576 A | * | 7/2000 | Sunshine et al. .......... 73/29.01 |
| 6,171,378 B1 | | 1/2001 | Manginell .................. 96/143 |
| 6,194,769 B1 | | 2/2001 | Martin .................. 257/414 |

OTHER PUBLICATIONS

Webster's II, New Riverside University Dictionary. (1994).*
Z. Zhang, M.J. Yang and J. Pawliszyn, "Solid–Phase Microextraction," *Analytical Chemistry*, vol. 66, pp. 844A—853A, Sep. 1, 1994.
N.K. Raman, M.T. Anderson and C.J. Brinker, "Template–Based Approaches to the Preparation of Amorphous, Nanoporous Silicas," *Chemistry of Materials*, vol. 8, pp. 1682–1701, 1996.

(Continued)

*Primary Examiner*—Jill Warden
*Assistant Examiner*—Brian Sines
(74) *Attorney, Agent, or Firm*—John P. Hohimer (57) ABSTRACT

A chemical-sensing apparatus is formed from the combination of a chemical preconcentrator which sorbs and concentrates particular volatile organic chemicals (VOCs) and one or more chemiresistors that sense the VOCs after the preconcentrator has been triggered to release them in concentrated form. Use of the preconcentrator and chemiresistor(s) in combination allows the VOCs to be detected at lower concentration than would be possible using the chemiresistor(s) alone and further allows measurements to be made in a variety of fluids, including liquids (e.g. groundwater). Additionally, the apparatus provides a new mode of operation for sensing VOCs based on the measurement of decay time constants, and a method for background correction to improve measurement precision.

33 Claims, 4 Drawing Sheets

OTHER PUBLICATIONS

M.P. Eastman, R.C. Hubhes, G. Yelton, A.J. Ricco, S.V. Pate, and M.W. Jenkins, "Application of the Solubility Parameter Concept to the Design of Chemiresistor Arrays," *Journal of the Electrochemical Society*, vol. 146, pp. 3907–3913, 1999.

Y. Lu, G. Cao, R.P. Kale, S. Prabakar, G.P. Lopez and C.J. Brinker, "Microporous Silica Prepared by Organic Templating: Relationship Between the Molecular Template and Pore Structure," *Chemistry of Materials*, vol. 11, pp. 1223–1229, 1999.

S.V. Patel, M.W. Jenkins, R.C. Hughes, W.G. Yelton and A.J. Ricco, "Differentiation of Chemical Components in a Binary Solvent Vapor Mixture Using Carbon/Polymer Composite–Based Chemiresistors," *Analytical Chemistry*, vol. 72, pp. 1532–1542, Apr. 1, 2000.

R.C. Hughes, S.A. Casalnuovo, K.O. Wessendorf, D.J. Savignon, S. Hietala, S.V. Patel and E.J. Heller, "Integrated Chemiresistor Array for Small Sensor Platforms," *Detection and Remediation Technologies for Mines and Minelike Targets V, Proceedings of the SPIE*, vol. 4038, pp. 519–529, Apr. 24–28, 2000.

R.C. Hughes, S.V. Patel and R.P. Manginell, "A MEMS Based Hybrid Preconcentrator/Chemiresistor Chemical Sensor," Paper presented at the 198th Meeting of The Electrochemical Society, Phoenix, AZ, Oct. 22–27, 2000.

* cited by examiner

APPARATUS FOR SENSING VOLATILE ORGANIC CHEMICALS IN FLUIDS

GOVERNMENT RIGHTS

This invention was made with Government support under Contract No. DE-AC04-94AL85000 awarded by the U.S. Department of Energy. The Government has certain rights in the invention.

FIELD OF THE INVENTION

The present invention relates in general to chemical sensing, and in particular to an apparatus that utilizes a chemical preconcentrator to extract volatile organic chemicals (VOCs) from a fluid and to generate a concentrated whiff of the VOCs for detection with one or more chemiresistors. The present invention has applications for identifying and characterizing VOCs for environmental monitoring, industrial process control, contraband detection, etc.

BACKGROUND OF THE INVENTION

Current methods for measuring volatile organic chemicals (VOCs) and other pollutants in the field generally involve sample collection and subsequent analysis in a well-equipped analytical chemistry laboratory. This process is time consuming and relatively expensive. For example, metropolitan water utility districts take thousands of water samples each year and perform tens of thousands of tests on those samples to determine the quality of the water (i.e. whether it meets current drinking water standards), and to check for potentially harmful substances. Additionally, tens of thousands of sites containing toxic chemical spills, leaking underground storage tanks, and chemical waste dumps require accurate characterization and long-term monitoring to reduce health risks and ensure public safety.

There exists a need for rapid, simple on-site analysis capability with high sensitivity and selectivity for detecting particular VOCs in fluids (e.g. air and ground water). The present invention provides an advance in the art to address this need by providing, in combination, a chemical preconcentrator which selectively sorbs (i.e. absorbs or adsorbs) VOCs from a liquid, gas or vapor and which, upon command, can subsequently release the absorbed or adsorbed VOCs in a concentrated whiff (i.e. a puff or plume) so that one or more chemiresistors (defined herein as chemically-sensitive resistors wherein the resistance varies in proportion to one or more chemical species to which the chemically-sensitive resistors are exposed) can detect and characterize particular VOCs in the concentrated whiff.

An advantage of the present invention is that an improved sensitivity and selectivity for sensing of VOCs is provided by the combination of the chemical preconcentrator and the chemiresistor(s) as compared to the use of chemiresistors alone.

Another advantage is that background correction for the response of the chemiresistor(s) is simplified by providing the VOCs to the chemiresistor(s) in a concentrated whiff over a short period of time.

A further advantage of the present invention is that the chemical preconcentrator can be separated from and located distal to the chemiresistor(s) to accumulate a VOC sample from a fluid, and then can be brought into proximity to the chemiresistor(s) for the analysis of particular VOCs in the sample.

Yet another advantage of the present invention is that particular VOCs can be identified and characterized based on a decay time constant using the apparatus of the present invention.

These and other advantages of the present invention will become evident to those skilled in the art.

SUMMARY OF THE INVENTION

The present invention relates to an apparatus for sensing an analyte (also referred to herein as a volatile organic chemical or a chemical species of interest) in a fluid which comprises a chemical preconcentrator and one or more chemiresistors. The chemical preconcentrator further comprises a sorptive material and a heating element, with the sorptive material acting to sorb (i.e. absorb or adsorb) the analyte from the fluid over time, and with the heating element upon electrical activation releasing the analyte from the sorptive material in concentrated form (e.g. as a whiff of concentrated analyte). The concentrated analyte can be detected by at least one chemiresistor located proximate to the chemical preconcentrator, with each chemiresistor having an electrical resistance that changes in response to exposure to the concentrated analyte, thereby sensing the analyte. The term "sensing" as used herein can refer to detecting the presence of a particular chemical of interest in the fluid, or quantifying an amount of the chemical of interest in the fluid (e.g. a liquid, vapor or gas), or both. The chemical-sensing apparatus of the present invention can further include a resistance measurement unit for measuring a change in the electrical resistance of the chemiresistor upon exposure to the concentrated analyte.

The sorptive material preferably comprises a polymer or sol-gel coating, and can optionally include fine-grain particles of activated charcoal (also termed activated carbon) or fine-grain particles of a carbon molecular sieve material to enhance absorption or adsorption of the analyte. The heating element preferably comprises a resistive heating element.

The chemical preconcentrator is formed on a substrate, with the sorptive material and the heating element being located on a thinned portion of the substrate. Additionally, one or more chemiresistors can be located on the same substrate as the chemical preconcentrator, or on different substrates. When different substrates are used for the chemical preconcentrator and the chemiresistor(s), the two substrates can be arranged substantially coplanar (i.e. side by side); or alternately the two substrates can be arranged one above the other with the chemiresistor facing the sorptive material of the chemical preconcentrator.

Each chemiresistor comprises a chemiresistive material disposed between at least one pair of spaced-apart electrodes. The chemiresistive material comprises a plurality of electrically-conductive particles (e.g. carbon or metal) suspended in a polymer host material, with the electrically-conductive particles generally comprising 20–40 percent by volume of the chemiresistive material. The polymer host material, which is selected to provide a high sensitivity for absorption or adsorption of a particular analyte, can comprise, for example, poly(n-vinyl pyrrolidone), poly (vinyl alcohol), poly(ethylene-vinyl acetate) or poly (isobutylene).

The present invention further relates to a chemical-sensing apparatus that comprises a chemical preconcentrator having a sorptive material for sorbing a chemical species of interest from a fluid (e.g. a liquid, gas or vapor) over time and subsequently releasing the chemical species of interest upon heating of the sorptive material, and one or more chemiresistors located proximate to the chemical preconcentrator for sensing the chemical species upon heating of the sorptive material. The sorptive material can comprise activated charcoal or a carbon molecular sieve material, and can further comprise a polymer or sol-gel host material wherein the activated charcoal or carbon molecular sieve material is embedded. Each chemiresistor comprises a plurality of electrically-conductive particles (e.g. carbon or metal) suspended in a polymer host material. Examples of polymer host materials which can be used to form the chemiresistor(s) include poly(n-vinyl pyrrolidone), poly (vinyl alcohol), poly(ethylene-vinyl acetate) and poly (isobutylene).

The present invention also relates to a method for increasing the sensitivity for detection of an analyte in a fluid using at least one chemiresistor. This method comprises steps for providing a sorptive material and sorbing the analyte from the fluid into the sorptive material, and heating the sorptive material in the proximity of the chemiresistor, thereby generating a concentrated whiff (i.e. a puff or plume) of the analyte for detection by the chemiresistor. By providing a concentrated whiff of the analyte to one or more chemiresistors, the present invention allows the detection of a much lower concentration of the analyte than would be possible using the chemiresistors alone.

In some embodiments of the present invention, the step for sorbing the analyte from the fluid into the sorptive material can be performed at a location distal to the chemiresistor. In this way only the sorptive material need be exposed to the fluid (e.g. ground water or a high-relative-humidity environment) containing the analyte. Once the sorptive material has been loaded with the analyte to be sensed, the sorptive material can be reunited with the chemiresistor(s) in a common housing prior to heating the sorptive material for sensing of the analyte by the chemiresistor(s).

The method can further include steps for measuring a resistance of the chemiresistor immediately prior to the step for heating the sorptive material, and then comparing this measured resistance with the resistance measured upon heating of the sorptive material to provide a background-corrected measurement of the analyte. The method of the present invention can also include a step for characterizing the analyte by measuring a decay time constant for a change in resistance of the chemiresistor after exposure to the concentrated whiff of the analyte.

Additional advantages and novel features of the invention will become apparent to those skilled in the art upon examination of the following detailed description thereof when considered in conjunction with the accompanying drawings. The advantages of the invention can be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1:
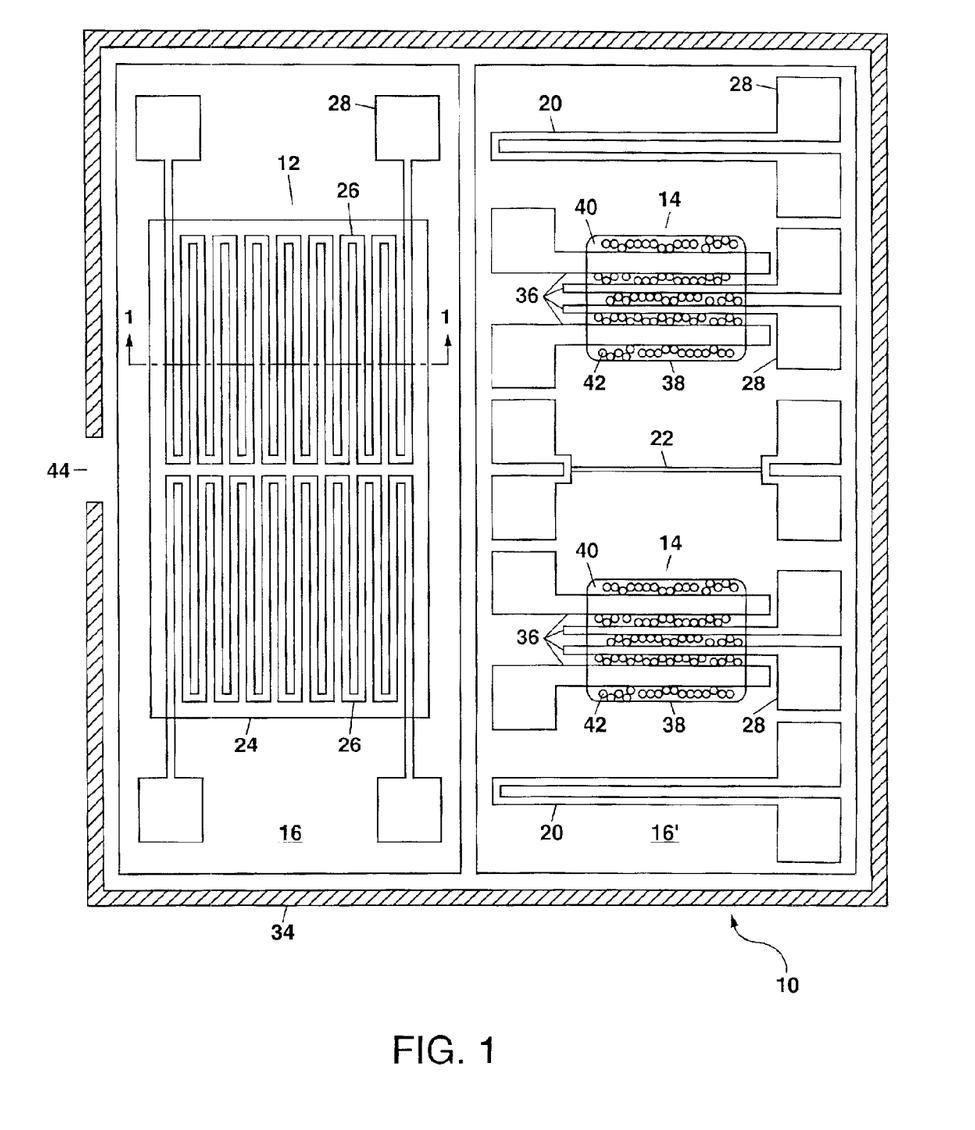
FIG. 1 schematically illustrates in plan view a first embodiment of the present invention.

Referring to FIG. 1, there is shown a first embodiment of the chemical-sensing apparatus 10 of the present invention. In FIG. 1, the apparatus 10 comprises a chemical preconcentrator 12 and a plurality of chemiresistors 14. The term "chemiresistor" as used herein refers to a resistor whose electrical resistance changes (e.g. increases) upon exposure to molecules of one or more chemical species. Although the preconcentrator 12 and the chemiresistors 14 are shown in FIG. 1 as being located on different substrates 16 and 16', in other embodiments of the present invention a common substrate 16 can be used to support both the preconcentrator 12 and one or more chemiresistors 14.

The substrates 16 and 16' in FIG. 1 each comprise monocrystalline silicon, with a thickness of generally about 0.5 millimeter. An insulating layer 18 (e.g. silicon nitride, silicon dioxide, silicon oxynitride, silicate glass or silicon carbide) can be formed above an upper surface of each substrate 16 and 16' to electrically isolate the preconcentrator 12, the chemiresistors 14 and other elements (e.g. one or more substrate heaters 20 and a temperature sensor 22, or electronic circuitry optionally formed on the substrates 16 or 16') from the substrates 16 and 16' when the substrates 16 and 16' are doped for electrical conductivity (see FIG. 2). In other embodiments of the present invention other materials can be used for one or both of the substrates 16 and 16' including other types of semiconductors (e.g. gallium arsenide), dielectric materials (e.g. glass, crystalline quartz, fused silica, plastic, resin or ceramic) or metals. Since the dielectric materials above are electrically insulating, the insulating layer 18 can be omitted when one or both of the substrates 16 and 16' comprise a dielectric material, or alternately when a semi-insulating semiconductor substrate is used. The term "substrate" as used herein is intended to include the insulating layer 18, if present.

The preconcentrator 12, which is formed on a monocrystalline silicon substrate 16 in the embodiment of the present invention in FIG. 1, comprises a sorptive material 24 overlying one or more heating elements 26. Further details of the preconcentrator 12 can be seen in the cross-section view in FIG. 2 taken along the section line 1—1 in FIG. 1.

Figure 2:
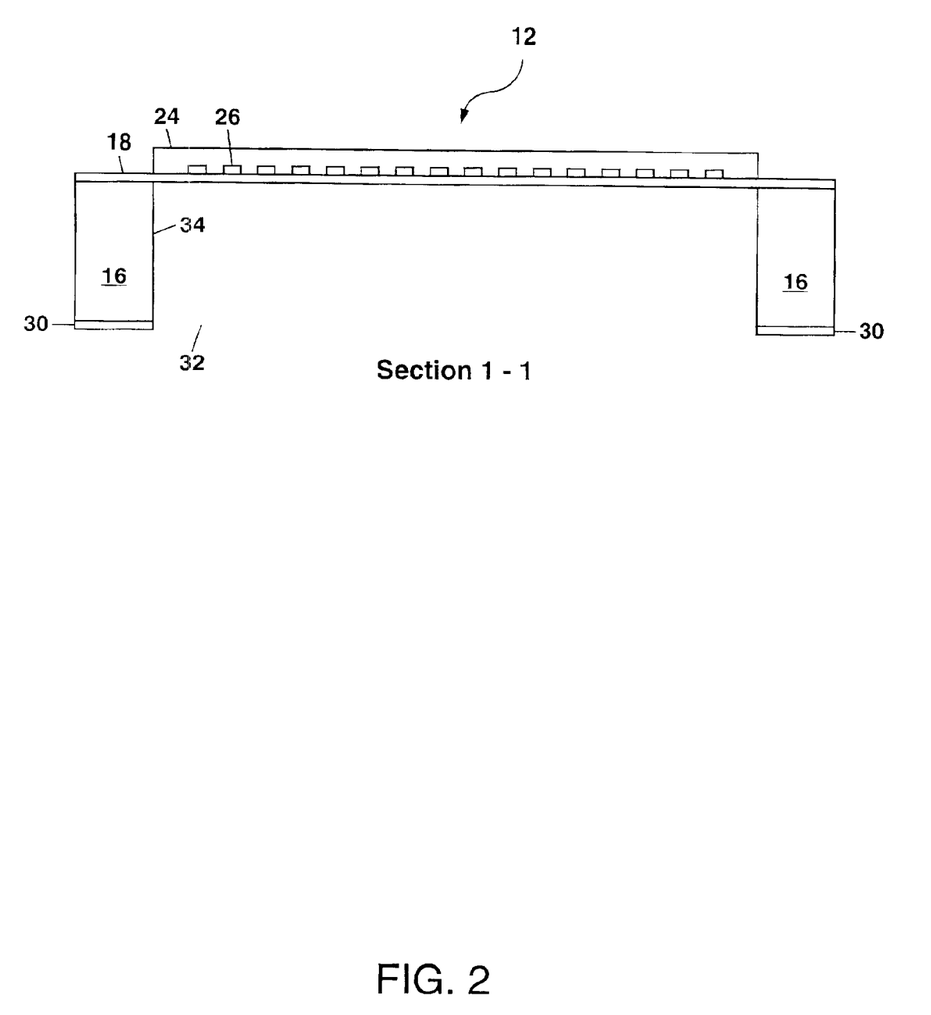
FIG. 2 shows a schematic cross-section view of the chemical preconcentrator along the section line 1—1 in FIG. 1.

In FIG. 2, the substrate 16 is locally thinned underneath the heating elements 26 and the sorptive material 24 to allow a rapid heating of the sorptive material 24 without substantial thermal conduction (i.e. heat loss) to the substrate 16. This minimizes the amount of electrical power required to heat the sorptive material 24 to an elevated temperature (e.g. 150–200° C.), decreases a response time for heating to only a few milliseconds, and minimizes heat transfer to the adjacent chemiresistors 14. The local thinning of the substrate 16 is generally performed after first forming the heating element 26 and the sorptive material 24 on an upper surface of the substrate 16.

The silicon substrate 16 in FIG. 2 is initially prepared by forming a sub-micron thickness of thermal oxide over each surface of the substrate 16 at high temperature. The substrate 16 can then be coated on both sides with a 0.5–1 μm layer of low-stress silicon nitride deposited by low-pressure chemical vapor deposition (LPCVD) to form the insulating layer 18 on the upper surface of the substrate 16. The low stress silicon nitride on a lower surface of the substrate 16 will later be patterned to form an etch mask 30.

The heating element 26 is formed on the upper surface of the substrate 16 by depositing and patterning one or more layers of metal. For example, to form a platinum heating element 26, a thin (e.g. 15–20 nm) layer of titanium followed by a thicker (e.g. 100 nm) layer of platinum can be deposited on the substrate 16 and insulating layer 18 and patterned by etching or lift-off to form a boustrophedon (i.e. meandering or serpentine) pattern for the heating element 26 as shown in FIG. 1.

Once formed, the heating element 26 can be annealed, if needed, to reduce any residual stress therein. This can be done, for example, at a temperature of about 500° C. in a nitrogen ambient for one-half hour. Bond pads 28 can be formed at the ends of the boustrophedon heating element 26 by deposition of the above titanium layer followed by a 100-nm-thick gold layer which can be patterned by etching or lift-off (e.g. using another patterned photoresist mask which can be stripped to remove the gold outside the bond pads 28). Typical operating voltages for each heating element 26 in FIG. 1 are generally in the range of 5–20 volts.

An optional heat-spreading layer (not shown) can be formed over each heating element, if desired, to improve heating uniformity. This can be done by blanket depositing an overlayer of about 100–200 nm silicon nitride followed by deposition of about 200 nm of aluminum, gold or polycrystalline silicon.

The various layers forming the heating element 26 and the optional heat-spreading layer can then be protected during a step for locally thinning the substrate 16 in a region wherein the sorptive material 24 is later to be deposited. This can be done by depositing an etch-resistant protection layer (not shown) over the upper surface of the substrate 16. The protection layer can comprise, for example, several microns of photoresist spun-on over the upper surface of the substrate 16.

The layer of silicon nitride (about 1 µm thick) covering the lower surface of the substrate 16 can then be patterned to form an etch mask 30 for locally thinning the substrate 16 by etching. Those skilled in the art will understand that the term "patterning" as used herein refers to a sequence of well-known integrated circuit (IC) process steps including applying a layer of photoresist on the substrate 16 or 16', prebaking the photoresist layer, aligning the substrate 16 or 16' to a photomask (i.e. a reticle), exposing the photoresist through the photomask, developing the photoresist, baking the photoresist, etching away surfaces not protected by the photoresist or lifting-off material layers deposited over the photoresist, and stripping the photoresist so that further processing can take place. In some instances a hard mask (e.g. comprising silicon nitride or a silicate glass) can be substituted for the photoresist to provide greater resistance to etching.

In FIG. 2, the silicon nitride etch mask 30 is patterned to provide a shaped opening 32 therethrough that is equal to or slightly larger than the size and shape of the sorptive material 24 which will later be deposited on the upper surface of the substrate 16. This shaped opening 32 allows a selective etchant to remove an exposed portion of the substrate 16 by etching inward from the lower surface of the substrate 16. The selective etchant can comprise an anisotropic wet etchant such as potassium hydroxide (KOH), tetramethyl ammonium hydroxide (TMAH) or ethylenediamine pyrocatechol (EDP) which selectively removes the monocrystalline silicon substrate material and which terminates etching on (111) crystallographic planes of the silicon. This can produce angled sidewalls 34 for the portion of the substrate 16 which is thinned when a (100)-oriented silicon substrate 16 is used; whereas the sidewalls 34 will be straight (i.e. substantially perpendicular to the upper surface of the substrate 16) when a (110)-oriented silicon substrate 16 is used. Another method which can be used to produce straight sidewalls 34 as shown in FIG. 2 is to use an anisotropic dry etching method.

An example of the anisotropic dry etching method which can be used to locally thin the substrate 16 is that commonly referred to as the "Bosch process" and which is detailed in U.S. Pat. No. 5,501,893 to Laermer, which in incorporated herein by reference. Briefly, the "Bosch process" utilizes multiple anisotropic etching steps performed by reactive ion etching combined with simultaneous deposition of an isotropic polymer/inhibitor to minimize lateral etching. When using the "Bosch process" for etching the substrate 16, the etching can be terminated before etching completely through the silicon substrate material; and a wet etching step (e.g. with KOH) can be used to remove the remaining silicon substrate material, with the silicon nitride insulating layer 18 acting as an etch stop. This prevents reactive ion etching of the silicon nitride insulating layer 18 which forms a suspended membrane covering the etched portion of the substrate 16.

To complete formation of the preconcentrator 12, the protection layer covering the heating element 26 can be removed, and the sorptive material 24 can be formed over the heating element 26. The sorptive material 24, which can be applied as one or more layers having a total thickness of, for example, 10–50 microns and an area of, for example, 0.04 cm$^2$, comprises a polymer or sol-gel material which has been selected to provide an affinity for sorbing one or more analytes.

In the case of a polymer sorptive material 24, a particular polymer used to form the sorptive material 24 can be selected on the basis of its solubility parameter, $\delta$, which is preferably about the same as the solubility parameter for the analyte to be sorbed into the material 24. When the solubility parameters, $\delta$, of the sorptive material and analyte are about the same, there will be a substantial interaction between molecules of the sorptive material 24 and the analyte, thereby leading to a substantial sorption of the analyte into the sorptive material 24. Solubility parameters, $\delta$, for various polymers and analytes can be determined from simple experiments, can be readily computed, or can be determined from tables in chemical reference books (see e.g. E. A. Grulke, in *Polymer Handbook,* 3rd edition, J. Brandrup and E. H. Immergut, eds., p. VII, 519, John Wiley & Sons, New York, 1989; A. F. M. Barton, *CRC Handbook of Solubility Parameters and Other Cohesion Parameters,* CRC Press, Boca Raton, Fla., 1983; M. P Eastman et al, "Application of the Solubility Parameter Concept to the Design of Chemiresistor Arrays," *Journal of the Electrochemical Society,* vol. 146, p. 3909, 1999). Solubility parameters, $\delta$, for virtually all polymers and VOCs range between a low value of 14 MPa$^{1/2}$ for isooctane to a high value of 48 MPa$^{1/2}$ for water.

The solubility parameter, $\delta$, for a given polymer or VOC is loosely related to the cohesive energy and thus the attractive strength among the molecules of the material. The solubility parameter, $\delta$, was originally conceived to describe the free energy of mixing of nonpolar, nonassociating fluids, but has been extended to other polymers and VOCs. A VOC and a polymer that have about the same value of $\delta$, are miscible so that the VOC can be easily and quickly sorbed into the polymer and subsequently desorbed upon heating of the polymer.

Polydimethylsiloxane is an example of a polymer that can be used to form the sorptive material 24. The polydimethylsiloxane can further be embedded with fine-ground activated charcoal (e.g. with a particle size of 20–50 μm or less) or a fine-ground high-surface-area carbon molecular sieve material (with the same particle size of 20–50 μm or less) to enhance the sorption of VOCs into the sorptive material 24. The polydimethylsiloxane can be prepared in liquid form as an ink-like fluid by dissolution into a suitable solvent with or without the activated charcoal or carbon molecular sieve material mixed therein; and then this ink-like fluid can be coated onto the substrate 16 (e.g. by spin coating, spray coating, inkjet deposition, etc.) and dried or cured to form the sorptive material 24 shown in FIGS. 1 and 2. An advantage of using a sorptive material 24 comprising polydimethylsiloxane is that this particular sorptive material does not appreciably concentrate (i.e. sorb) water vapor or ethanol so that it can be used to extract VOCs from an ambient wherein the relative humidity is high, or where ethanol is present.

A sorptive material 24 comprising a sol-gel oxide (also termed herein a sol-gel) can be substituted for the polymer sorptive material 24 in some embodiments of the present invention. Such a sol-gel sorptive material 24 can be formed, for example, using a surfactant templated formation process as is well-known in the art (see e.g. N. K. Raman et al, "Template-Based Approaches to the Preparation of Amorphous, Nanoporous Silicas," *Chemistry of Materials.* vol. 8, pp.1682–1701, 1996; Y. Lu et al, "Microporous Silica Prepared by Organic Templating: Relationship Between the Molecular Template and Pore Structure, *Chemistry of Materials,* vol. 11, pp.1223–1229, 1999; see also U.S. Pat. Nos. 5,770,275 and 6,171,378 which are incorporated herein by reference).

Returning to FIG. 1, one or more chemiresistors 14 are located on a different substrate 16' which is assembled into a housing 34 (also termed a package) alongside the preconcentrator 12. The substrate 16' can also comprise monocrystalline silicon overcoated with an insulating layer (e.g. 100–200 nm of low-stress silicon nitride deposited by LPCVD). In other embodiments of the present invention, the substrate 16' can comprise other semiconductor or dielectric materials as described previously with reference to the substrate 16.

Each chemiresistor 14 comprises one or more pairs of spaced-apart electrodes 36 with a chemiresistive material 38 disposed between the spaced-apart electrodes 36 and in electrical contact with the electrodes 36. Each electrode 36 is further connected at one end thereof to a bond pad 28 as shown in FIG. 1 so that electrical connections to an external resistance measurement unit 46 can be made (see FIG. 4).

The electrodes 36 in FIG. 1 can comprise a chemically-resistant metal or metal alloy. In particular, platinum can be used for the electrodes 36 since it is resistant to chemical attack by most chemicals including VOCs and water vapor. Additionally, the use of platinum for the electrodes 36 is advantageous since this metal can also be used to form a temperature sensor 22 and one or more heaters 20 on the substrate 16' using the same metal deposition and patterning steps used to form the electrodes 36. Furthermore, the use of platinum can allow the preconcentrator 12 and one or more chemiresistors 14 to be formed on a common substrate using the same deposition and patterning steps described previously for forming the preconcentrator heating elements 26 to also form the electrodes 36, the temperature sensor 22 and any substrate heaters 20 at the same time thereby reducing manufacturing and packaging costs.

When platinum is used to form the electrodes, an underlying adhesion layer of titanium (e.g. 15–20 nm thick) is generally used. The titanium and platinum can be deposited by evaporation or sputtering, with the thickness of the platinum being, for example, 100 nanometers. The electrodes 36 can comprise an inner pair of electrodes 36 about 10 μm wide and spaced apart by 50–100 μm, and an outer pair of electrodes 36 about 50 μm wide and spaced apart by 2–3 times the spacing of the inner pair of electrodes 36. The bond pads 28 connected to one end of each electrode 36 can be formed as previously described for the preconcentrator 12.

The chemiresistive material 38 in FIG. 1 comprises a polymer host material 40 and further includes a plurality of electrically-conductive particles 42 (e.g. carbon or metal particles such as silver) embedded within the polymer host material 40. Carbon particles 42 are preferably used in the embodiment of the present invention in FIG. 1;

and these particles 42 can be, for example, in the form of graphitized carbon with a sub-micron particle size (e.g. 20–30 nm). In FIG. 1, for clarity, the electrically-conductive particles 42 are shown greatly enlarged and are further shown only between the electrodes 36, although those skilled in the art will understand that the particles 42 are uniformly distributed throughout the entire volume of the chemiresistive material 38.

The polymer host material 40 is preferably electrically nonconducting (i.e. insulating) while the electrically-conductive particles 42 provide multiple conduction pathways for an electrical current to flow when a voltage is applied between the spaced-apart electrodes 36. The polymer host material 40 used to form each chemiresistive material 38 can be selected to have a solubility parameter, δ, about the same as one or more analytes (i.e. VOCs) to be sensed by that chemiresistor 14. In this way, the polymer host material 40 will readily sorb these analytes thereby swelling the chemiresistive material 38 and increasing a spacing between adjacent of the electrically-conducting particles 42 which will increase the electrical resistance of the chemiresistor 14 and provide a means for detecting and quantifying the analytes. The responses of a plurality of chemiresistors 14 can be measured and correlated to distinguish between different analytes, especially when particular chemiresistors 14 are responsive to more than one analyte. Very large changes in resistance are possible when the volume of the chemiresistive material 38 is changed close to the percolation threshold, which is generally between 20 and 40% by volume of the electrically-conductive particles 42. The sorption process of the chemiresistors 14 is reversible so that the chemiresistors 14 can return to their initial state in a short time (e.g. minutes) when the concentrated whiff of the analytes has dissipated.

The chemiresistive material 38 can be prepared in liquid form by dissolving the polymer host material 40 and 20–40% by volume of the electrically-conductive particles 42 in a solvent (e.g. water, chlorobenzene or chloroform) having about the same solubility parameter, δ, as the polymer host material 40. Typically, 0.1 gram of the polymer host material 40 and electrically-conducting particles 42 (e.g. graphitized carbon) are dissolved in 5 milliliters of solvent. A non-ionic surfactant can also be added to this mixture to chemically bond to the electrically-conducting particles and thereby form steric barriers to prevent aggregation or agglomeration of these particles 42. The provision of a non-ionic surfactant in the chemiresistive material 38 is also expected to increase the long-term stability of the chemiresistors 14 by providing a more stable matrix for the electrically-conductive particles 42 and by preventing migration of the electrically-conducting particles 42 toward the electrodes 36 which could otherwise lead to aggregation and thereby change the resistance of the chemiresistors 14.

The liquid chemiresistive material 38 can then be sonicated (e.g. with multiple pulses from a point ultrasonic source) to disperse the electrically-conductive particles 42 throughout the material 38 and to prevent the formation of agglomerated colloids which might otherwise electrically short-circuit the narrowly-spaced electrodes 36. Filtering (e.g. with a 5 µm pore size filter) can also be used, if necessary, to remove any agglomerated colloids formed by the electrically-conductive particles 42 prior to spin coating or dispensing the chemiresistive material 38 onto the substrate 16' over the spaced-apart electrodes 36. Precise dispensing of the chemiresistive material 38 can be performed using a commercial automated dispensing unit (e.g. an Asymtek Century Corporation, Model C-702 Automated Dispensing Unit with a Model 740V Low Viscosity Attachment) using a small-gauge needle.

The chemiresistive material 38 is then dried at room temperature under ambient conditions to solidify the polymer host material 40 with the embedded electrically-conducting particles 42 therein. The thickness of the chemiresistive material 38 after drying is generally less than about 10 µm and preferably on the order of 1 µm or less to provide a fast response time for sorption of the analyte into the chemiresistive material 38 in order to sense the analyte. The width of the chemiresistive material 38 can exceed the spacing between the outer pair of electrodes 36 in FIG. 1 and can be, for example, about 500 µm, with the length of the chemiresistive material 38 being, for example, 2–3 mm long. After formation, the chemiresistors 14 can be qualified for use by measuring the electrical resistance which is generally in the range of about one kiloOhm to one megaOhm depending upon the dimensions of the chemiresistors 14 and the volume fraction of the electrically-conductive particles 42.

In the embodiment of the present invention shown in FIG. 1, multiple chemiresistors 14 can be provided on the substrate 16' to sense many different types of VOCs (e.g. xylene, trichloroethylene, isooctane, kerosene, methyl t-butyl ether, methyl salicylate). The term "sense" as used herein means detecting the presence of a particular analyte as well as quantifying the relative or absolute concentration of that analyte in a fluid.

Each chemiresistor 14 can have a polymer host material 40 with a different solubility parameter, δ, for responsivity to a different VOC or class of VOCs having about the same solubility parameter. In this way, a relatively small number of chemiresistors 14 (e.g. four chemiresistors 14) can suffice to detect the presence of virtually any VOC. Particular polymer host materials 40 that can be used to form the chemiresistors 14 in the apparatus 10 of the present invention include poly(n-vinyl pyrrolidone) (also termed PNVP), poly(vinyl alcohol) (also termed PVA), poly(ethylene-vinyl acetate) (also termed PEVA), and poly(isobutylene) (also termed PIB). PIB is useful for detecting VOCs having low values of the solubility parameter, δ, which include nonpolar VOCs; whereas PVA is useful for detecting VOCs having larger values of δ (e.g 25–20 MPa$^{1/2}$) which include polar VOCs (e.g. methanol). Various compositions of the PVA are possible depending upon the extent of hydroxylation which is generally in the range of 75–98%.

The four polymer host materials 40 listed above can be used to detect a large variety of VOCs. Other polymer host materials 40 that can be used according to the present invention include ethyl cellulose (also termed EC), poly (diphenoxyphosphazine) (also termed PDPP) and poly-epichlorohydrin (also termed PECH). Those skilled in the art will understand that a polymer host material 40 can be selected to provide a high sensitivity or selectivity for detection of a particular VOC by matching the solubility parameter, δ, of the polymer host material 40 with that of the VOC to be sensed as described previously.

Since each chemiresistor 14 is responsive to analytes having about the same solubility parameter, δ, multiple chemiresistors 14 can be provided as an array to produce different and varied responses to each analyte thereby providing an effective means for discriminating against interfering analytes to detect and quantify one or more analytes of interest. The response produced by each chemiresistor 14 is in the form of a change in electrical resistance which occurs when the chemiresistive material 38 swells upon sorption of one or more VOCs and thereby breaks some of the conductive pathways formed by the electrically-conductive particles 42.

The use of two pair of electrodes 36 and associated bond pads 28 as shown in FIG. 1 allows the use of a four-point measurement of the resistance of the each chemiresistor 14 to provide an accurate measurement of the resistance of the chemiresistive material 38 and to compensate for effects due to contact resistance, which can also change upon swelling of the polymer host material 40. A four-point resistance measurement is also advantageous for compensating for lead resistance in wiring 48 connecting the apparatus 10 to an external resistance measurement unit 46 (see FIG. 4).

The resistance measurement unit 46 can comprise any apparatus capable of measuring electrical resistance, including an ohmmeter, a multimeter, a data logger, a current/voltage measurement system. Those skilled in the art will understand that resistance is defined as a voltage drop across an electrical element divided by an electrical current flowing through that element so that a measurement of resistance can be performed by either flowing a known electrical current through the element and measuring the resultant voltage drop across the element or by applying a known voltage across the element and measuring the resultant current flowing through the element. The resistance measurement unit 46 can further include a computer for automated control of the apparatus 10 and for data acquisition from one or more chemiresistors 14. In some embodiments of the present invention, the resistance measurement unit 46 can be formed on the substrate 16' alongside the chemiresistors 14 as an integrated circuit.

A common source of interference in detecting or quantifying particular analytes using the apparatus 10 of FIG. 1 is due to relative humidity (i.e. moisture) in the ambient environment. The presence of or changes in moisture (i.e. water vapor) will affect most strongly those chemiresistors 14 having a polymer host material 40 with a high value of δ (e.g. a material 40 comprising PVA). Compensation for the effect of relative humidity can be performed by selecting a plurality of chemiresistors 14 having widely-varying values of the solubility parameter, δ, so that one or more of the chemiresistors 14 are responsive to relative humidity while other chemiresistors 14 are relatively immune to relative humidity. Each chemiresistor 14 can also be responsive to one or more VOCs of interest. Suitable pattern recognition algorithms known to the art can then be used to analyze the responses of the chemiresistors 14 to various VOCs and interfering vapors and sort out any effects of relative humidity on the measurements (see e.g., S.V. Patel et al, "Differentiation of Chemical Components in a Binary Solvent Vapor Mixture Using Carbon/Polymer Composite-Based Chemiresistors," *Analytical Chemistry,* vol. 72, pp. 1532–1542, 2000).

Additionally, thermal expansion or contraction due to temperature changes can change the electrical resistance of the chemiresistor 14 so that a temperature sensor 22 is preferably provided on the substrate 16' for sensing the temperature of the substrate 16' in order to provide compensation for the chemiresistors 14. The temperature sensor 22 can also compensate for any heating of the substrate 16' and chemiresistors 14 by the preconcentrator heating element 26.

The temperature sensor 22 can comprise a platinum resistance temperature sensor formed during the same metal deposition and patterning steps used to form the spaced-apart electrodes 36 in the chemiresistors 14. The platinum resistance temperature sensor 22 can comprise a linear or meander-line (i.e. boustrophedon) trace disposed between one or preferably two pair of bond pads 28 to provide a predetermined resistance (e.g. about 1 kiloOhm). The use of two pair of bond pads 28 electrically connected to the to the resistance temperature sensor 22 allows the use of a four-point measurement of the resistance of the sensor 22 to provide an accurate measurement of the temperature of the substrate 16' independent of lead or contact resistance.

One or more substrate heaters 20 can also be provided on the substrate 16' to heat the substrate 16' to a predetermined temperature (e.g slightly above room temperature) and to maintain the chemiresistors 14 at this temperature. Heating the substrate 16' slightly above room temperature can also be advantageous to prevent any condensation of moisture onto the chemiresistors 14 when the relative humidity is high. The resistance temperature sensor 22 can further be used in a feedback loop configuration with the substrate heaters 20 for temperature control of the substrate 16' and chemiresistors 14 thereon.

The chemical-sensing apparatus 10 of FIG. 1 can be packaged within a housing 34 for use. Such a housing 34 can comprise, for example, a conventional integrated circuit (IC) package (e.g. a dual-in-line package), with each substrate 16 and 16' being mounted on the IC package using an adhesive or solder, and with a plurality of electrical connections being made between the various bond pads 28 and pins on the IC package.

Various kinds of lids can be attached to the IC package to complete the housing 34. A demountable lid (e.g. comprising a cover glass) is useful in conjunction with the IC package for providing a very small dead volume (e.g. <0.03 $cm^3$) to confine an analyte sample desorbed from the preconcentrator 12 upon heating and thereby obtain a large signal from one or more chemiresistors 14 that subsequently detect the analyte in the sample.

Alternately, the housing 34 can include a covering or lid having one or more access openings 44 therein for admitting the fluid containing the analyte to be sensed. By providing these small (e.g. millimeter-size or smaller) access openings 44 in the housing 34, the fluid containing the analyte can diffuse into the housing 34 over time and be sorbed into the preconcentrator 12 which is generally at room temperature during this sorption process. The sorption process can go on for a time period from less than a minute to several hours or more depending on the concentration of the analytes in the fluid and a desired level of measurement sensitivity.

Once the analytes have been sorbed into the chemiresistive material 24, the heating element 26 can be activated to desorb the analytes to produce a concentrated whiff of analytes within the housing 34 for sensing the analytes. In this way, the apparatus 10 can be operated without the need for any pump or valves which are required with other types of chemical analysis systems (e.g. gas chromatography). The apparatus 10 of the present invention can thus provide a small size, low cost and low power alternative to more complicated and costly conventional chemical analysis systems.

In operation, the chemical preconcentrator 12 of the apparatus 10 is initially used to sorb and concentrate one or more analytes (e.g. VOCs) from a fluid to be analyzed over a period of time (e.g. minutes to hours). This is done simply by exposing the sorptive material 24 of the preconcentrator 12 to the fluid for a predetermined period of time. A relatively large number of analyte molecules can be accumulated in the preconcentrator 12 over time even from low analyte concentrations in the fluid because of the high porosity and retention of the sorptive material 24.

Once the analytes have been sorbed into the preconcentrator 12, an electrical current from a power supply (e.g. a direct-current power supply or a battery) can be passed through the heating element 26. The current rapidly heats the sorptive material 24 up to an elevated temperature sufficiently high (e.g. 150–200° C.) for desorption of the analytes from the sorptive material 24 as a concentrated whiff. The sorptive material 24 can be maintained at this elevated temperature for sufficient time for the chemiresistors 14 to sense the desorbed analytes (typically a few seconds to a few tens of seconds) and for the sorptive material 24 to be purged of the analyte. The sorptive material 24 reaches the elevated temperature in only a few milliseconds using a few hundred milliWatts (e.g. 100–300 mW) of electrical power.

The concentrated whiff (i.e. a puff or plume), which has a concentration of analyte molecules orders of magnitude larger than that present in the fluid, rapidly diffuses to the location of one or more chemiresistors 14 located on the substrate 16' a few millimeters away. Each chemiresistor 14 then sorbs certain of the analytes which are determined by the composition of the chemiresistive material 38, leading to a swelling of the chemiresistive material 38 and a resultant change in resistance which can be measured to provide an indication of the presence and quantity of particular analytes in the fluid. The resistance change produced in this way can be orders of magnitude larger than a background resistance change that occurs when the chemiresistors 14 directly measure an ambient concentration of the analytes in the fluid.

To compensate for changes in the resistance of the chemiresistors 14 over time due to variations in the ambient concentration of the analytes or due to a baseline drift of the chemiresistors 14, a timing signal can be derived from the electrical current provided to heat the preconcentrator 12 so that a change, $\Delta R$, in resistance, R, of the chemiresistors 14 can be measured only after the onset of heating of the preconcentrator 12. This change, $\Delta R$, which results from exposure of the chemiresistors 14 to the concentrated whiff of analytes, then provides a simple and effective method for background compensation and to correct for any changes in resistance of the chemiresistors 14 due to changes in ambient temperature, aging of the chemiresistive material 38, variations in the ambient concentration of the analytes, etc., thereby permitting an accurate measurement of one or more analytes in the fluid. The onboard temperature sensor 22 can be used to compensate for any transient heating of the substrate 16' produced as a result of heating the preconcentrator 12.

Additionally, use of the apparatus 10 of the present invention has revealed that different analytes can produce different response curves for the change in resistivity of the chemiresistors 14 upon exposure to the concentrated whiff of one or more analytes. This is thought to be due to different rates at which particular analytes are desorbed from the sorptive material 24 of the preconcentrator 12, sorbed into different compositions of the chemiresistive material 38 of the chemiresistors 14, and subsequently desorbed from the chemiresistive material 38. The result can be different time constants which are characteristic for particular combinations of analytes and chemiresistive material compositions which can be used to further aid in distinguishing between multiple analytes present within a given fluid sample.

Figure 3:
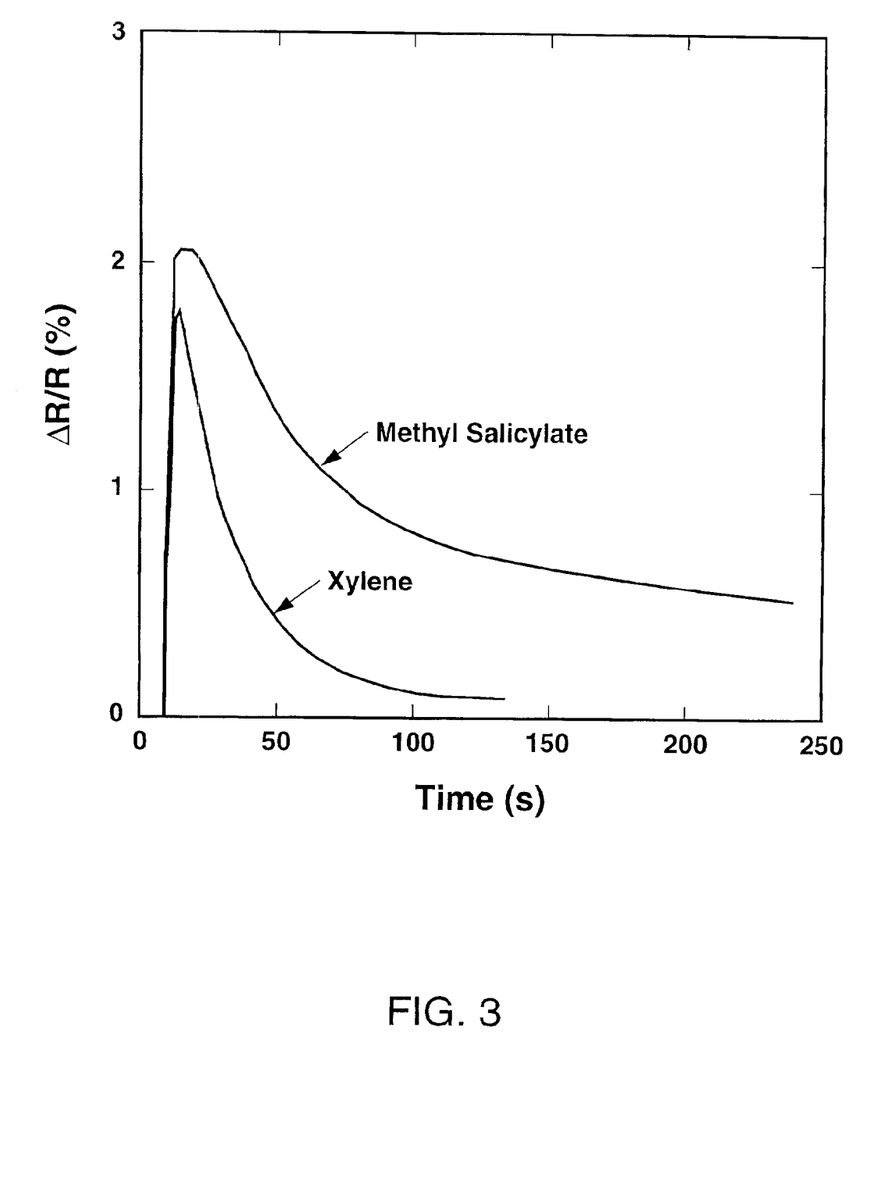
FIG. 3 shows normalized response curves for chemiresistors exposed to methyl salicylate and xylene to illustrate the difference in time constants which are characteristic of different analytes measured using the apparatus of the present invention.

FIG. 3 illustrates this for sensing of two analytes of interest, methyl salicylate and xylene, using the apparatus 10 of the present invention. In FIG. 3, measurements were performed separately for an ambient containing xylene and methyl salicylate at known concentrations, with each analyte being loaded into the preconcentrator 12 which was then heated to about 200° C. for three seconds. Heating of the preconcentrator 12 produced a rapid rise in the resistance of the chemiresistor 14 which sensed the concentrated whiff of methyl salicylate or xylene desorbed from the preconcentrator 12. After the three-second heating pulse, the preconcentrator 12 was turned off and the resistance of the chemiresistor 14 decayed towards its initial value representing the ambient concentration of methyl salicylate or xylene, with a decay time constant that is very different for the two measurements. In FIG. 3, the measured decay time constants for the normalized change in resistivity ($\Delta R/R$) for each chemiresistor 14 shows that methyl salicylate decays about three times slower than xylene. These decay time constants, or alternately measurements of the resistivity at different times during the heating pulse or after the preconcentrator 12 has been turned off, can be used as a further way of distinguishing between different VOCs with the apparatus 10. A table of the decay time constants can be constructed for many different VOCs and used as a way of identifying those VOCs in a sample of unknown or mixed composition using the apparatus 10 of the present invention.

Figure 4:
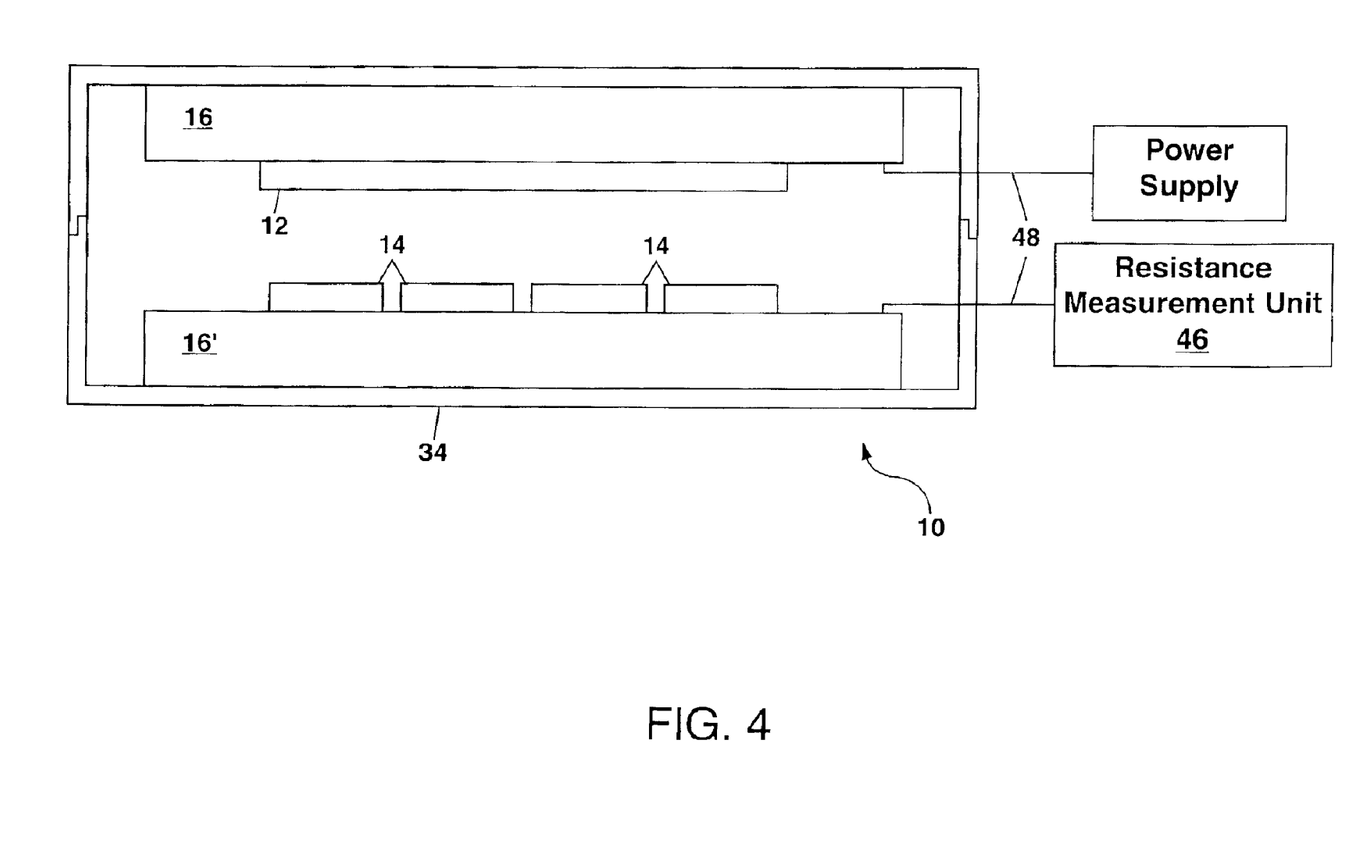
FIG. 4 schematically illustrates in cross-section view a second embodiment of the present invention.

FIG. 4 schematically illustrates in cross-section view a second embodiment of the apparatus 10 of the present invention. This embodiment of the present invention provides an increased measurement response time as compared to the embodiment of FIG. 1 since the chemiresistors 14 can be located even closer to the sorptive material 24 (e.g. $\leq 2$ millimeters), with the chemiresistors 14 preferably facing the sorptive material 24. This embodiment of the present invention also permits each of the preconcentrator 12 and one or more chemiresistors 14 to be located on different parts of a separable housing 34 so that the preconcentrator 12 can be separated from the chemiresistors 14 if desired. This can be advantageous, for example, when one or more analytes (e.g. VOCs) are to be measured in a liquid, in the vapor above a liquid (e.g. for groundwater monitoring), or in any environment incompatible with the chemiresistors 14. This can also be advantageous when the remainder of the housing 34 contains additional sensitive electronics such as circuitry for measuring the resistivity of the chemiresistors 14, a microcontroller with memory loaded with training sets of data for various VOCs and various levels of relative humidity, a display to indicate the composition of a measured VOC, etc. Exposure of the chemiresistors or other circuitry to the liquid or to the headspace of the liquid can be detrimental to the operation of the apparatus 10 since this can result in the accumulation of the liquid into the chemiresistive material 38 or circuitry through direct exposure or by condensation of moisture in a high-relative-humidity ambient. By separating the chemical preconcentrator 12 from the remainder of the separable housing 34, only the preconcentrator 12 need be exposed to the liquid or high-relative-humidity ambient.

Once removed, the portion of the separable housing 34 containing the preconcentrator 12 can be immersed into the liquid (e.g. ground water or a sample thereof) or high-relative-humidity ambient to sample VOCs emanating from the liquid or ambient. A wand (not shown) can optionally be attached to the portion of the housing 34 containing the preconcentrator 12 to aid in handling and positioning this portion in the liquid or ambient.

Additionally, the sorptive material 24 of the preconcentrator 12 can be tailored to exclude the liquid or condensed vapor (e.g. water) from the high-relative-humidity ambient, while still sorbing particular VOCs of interest from the liquid or ambient and concentrating these analytes within the preconcentrator 12. The preconcentrator 12 and housing portion can then be dried (e.g. by wiping or heating slightly above room temperature) and reunited with the remainder of the housing 34 to permit the desorption and measurement of the VOCs as previously described. In this way, the chemiresistors 14 and other sensitive electronic circuitry can be protected from exposure to the liquid while still permitting a measurement of the VOCs in the liquid, in a headspace directly above the liquid, or in a high-relative-humidity ambient.

The separable housing 34 in FIG. 4 can include a lip or O-ring seal so that the housing 34 can be sealed, if desired, during desorption of the analytes and sensing thereof. This can be useful, for example, to prevent exposure of an operator to the desorbed analytes (e.g. when the analytes are toxic or carcinogenic).

Other embodiments of the present invention are possible. For example, the placement of the chemiresistors 14 facing the preconcentrator 12 can be utilized in a housing 34 which includes one or more access openings 44 for admitting the fluid or analytes. This placement can be advantageous for reducing a response time of the apparatus 10 since the close spacing of the chemiresistors 14 to the preconcentrator 12 allow the desorbed analytes upon heating of the preconcentrator 12 to more rapidly reach the chemiresistors 14 than in the first embodiment of the present invention shown in FIG. 1.

The apparatus 10 of the present invention is useful for sensing many different and varied VOCs, including aromatic hydrocarbons like benzene, toluene, and xylene; chlorinated solvents like trichloroethylene (TCE); and aliphatic hydrocarbons like hexane and isooctane. These VOCs can be detected in water or the headspace over water for environmental ground water monitoring (e.g. to detect pollutants entering the ground water from chemical storage tanks, piping, or chemical waste dumps). Detection of particular VOCs can be at the part-per-million level, which for many VOCs of interest is below the drinking water standard. This detection level is too low for direct detection using the chemiresistors 14 alone without the preconcentrator 12. Additionally, the chemical-sensing apparatus 10 of the present invention is exceedingly simple in construction and use compared to conventional gas chromatography chemical analysis systems which require pumps and valves for operation.

Other applications and variations of the present invention will become evident to those skilled in the art. For example, the apparatus of the present invention can also be used to sense toxic vapors (e.g. phosphonates) or semi-volatile chemicals (e.g. high explosives or constituents thereof). As another example, the apparatus 10 of the present invention can be formed using other types of chemiresistors, including chemiresistors formed from field-structured composite materials as disclosed in U.S. Pat. No. 6,194,769 to Martin et al, which is incorporated herein by reference.

As yet another example, the apparatus 10 of the present invention can be formed as a self-contained unit including the preconcentrator 12 and one or more chemiresistors 14 together with integrated circuitry for powering the preconcentrator 12 and for sensing a change in resistance of the chemiresistors 14 and a power source (e.g. a battery). Such a self-contained unit 10 has applications for use as a warning system which can be located within a facility or worn by personnel as a "first responder badge" to indicate the presence of VOCs, high explosives, toxic vapors or other potentially hazardous chemicals. The circuitry in the warning system or "first responder badge" can trigger an integral audible or visible alarm, or both, to warn personnel of a potentially dangerous situation upon detecting the VOCs, high explosives, toxic vapors, etc. The warning system or "first responder badge" can also optionally include a readout of the concentration of the detected VOCs, high explosives, toxic vapors, etc., to provide further information of the danger presented to the personnel. In some cases, the circuitry can include memory to provide a record of personnel exposure thereby functioning as a dosimeter.

The matter set forth in the foregoing description and accompanying drawings is offered by way of illustration only and not as a limitation. The actual scope of the invention is intended to be defined in the following claims when viewed in their proper perspective based on the prior art.

What is claimed is:

1. An apparatus for sensing an analyte in a fluid, comprising:
   (a) a chemical preconcentrator further comprising a substrate, a sorptive material and a heating element both located on a thinned portion of the substrate, with the sorptive material acting to absorb or adsorb the analyte from the fluid over time, and with the heating element upon electrical activation releasing the analyte from the sorptive material in concentrated form; and
   (b) at least one chemiresistor located proximate to the chemical preconcentrator and spatially separated therefrom and having an electrical resistance that changes in response to exposure to the concentrated analyte, thereby sensing the analyte.

2. The apparatus of claim 1 further including a resistance measurement unit for measuring a change in the electrical resistance of the chemiresistor upon exposure to the concentrated analyte.

3. The apparatus of claim 1 wherein the sorptive material comprises a polymer or sol-gel coating.

4. The apparatus of claim 3 wherein the sorptive material further comprises fine-grain particles of activated charcoal or carbon molecular sieve material.

5. The apparatus of claim 1 wherein the heating element comprises a resistive heating element.

6. An apparatus for sensing an analyte in a fluid, comprising:
   (a) a chemical preconcentrator formed on a substrate and further comprising, a sorptive material and a heating element both located on a thinned portion of the substrate, with the sorptive material acting to absorb or adsorb the analyte from the fluid over time, and with the heating element upon electrical activation releasing the analyte from the sorptive material in concentrated form; and
   (b) at least one chemiresistor formed on the same substrate proximate to the chemical preconcentrator and spatially separated therefrom and having an electrical resistance that changes in response to exposure to the concentrated analyte, thereby sensing the analyte.

7. An apparatus for sensing an analyte in a fluid, comprising:
   (a) a chemical preconcentrator further comprising a substrate, a sorptive material and a heating element both located on a thinned portion of the substrate, with the sorptive material acting to absorb or adsorb the analyte from the fluid over time, and with the heating element upon electrical activation releasing the analyte from the sorptive material in concentrated form; and
   (b) at least one chemiresistor located proximate to the chemical preconcentrator on another substrate and having an electrical resistance that changes in response to exposure to the concentrated analyte, thereby sensing the analyte.

8. The apparatus of claim 7 wherein the substrates are located one above the other with the chemiresistor facing the sorptive material of the chemical preconcentrator.

9. The apparatus of claim 7 wherein the substrates are located proximate to each other and are substantially coplanar.

10. The apparatus of claim 1 wherein each chemiresistor comprises a chemiresistive material disposed between at least one pair of spaced-apart electrodes.

11. The apparatus of claim 10 wherein the chemiresistive material comprises a plurality of electrically-conductive particles suspended in a polymer host material.

12. An apparatus for sensing an analyte in a fluid, comprising:
   (a) a chemical preconcentrator further comprising a substrate, a sorptive material and a heating element both located on a thinned portion of the substrate, with the sorptive material acting to absorb or adsorb the analyte from the fluid over time, and with the heating element upon electrical activation releasing the analyte from the sorptive material in concentrated form; and
   (b) at least one chemiresistor located proximate to the chemical preconcentrator, with each chemiresistor comprising a chemiresistive material disposed between at least one pair of spaced-apart electrodes, with the chemiresistive material further comprising a plurality of electrically-conductive particles suspended in a polymer host material, with the electrically-conductive particles comprising 20–40 percent by volume of the chemiresistive material, and with each chemiresistor having an electrical resistance that chances in response to exposure to the concentrated analyte, thereby sensing the analyte.

13. The apparatus of claim 11 wherein the electrically-conductive particles comprise carbon.

14. The apparatus of claim 11 wherein the electrically-conductive particles comprise a metal.

15. The apparatus of claim 11 wherein the polymer comprises a polymer selected from the group consisting of poly(n-vinyl pyrrolidone), poly(vinyl alcohol), poly (ethylene-vinyl acetate) and poly(isobutylene).

16. A chemical-sensing apparatus, comprising:
   (a) a chemical preconcentrator further comprising a substrate with a sorptive material being located on a thinned portion of the substrate for sorbing a chemical species of interest from a fluid over time and subsequently releasing the chemical species of interest upon heating of the sorptive material; and (b) at least one chemiresistor located proximate to the chemical preconcentrator and spatially separated therefrom for sensing the chemical species upon heating of the sorptive material.

17. The apparatus of claim 16 further including a resistance measurement unit for measuring the resistance of each chemiresistor to determine the presence or concentration of the chemical species.

18. The apparatus of claim 16 wherein the fluid comprises a gas or vapor.

19. The apparatus of claim 16 wherein the fluid comprises a liquid.

20. The apparatus of claim 16 wherein the sorptive material comprises activated charcoal or a carbon molecular sieve material.

21. The apparatus of claim 20 wherein the sorptive material further comprises a polymer or sol-gel host material wherein the activated charcoal or the carbon molecular sieve material is embedded.

22. The apparatus of claim 16 wherein the chemiresistor comprises a plurality of electrically-conductive particles suspended in a polymer host material.

23. The apparatus of claim 22 wherein the electrically-conductive particles comprise carbon.

24. The apparatus of claim 22 wherein the electrically-conductive particles comprise a metal.

25. The apparatus of claim 22 wherein the polymer host material comprises a polymer selected from the group consisting of poly(n-vinyl pyrrolidone), poly(vinyl alcohol), poly(ethylene-vinyl acetate) and poly(isobutylene).

26. A method for increasing the sensitivity for detection of an analyte in a fluid using at least one chemiresistor, comprising steps for:

(a) providing a sorptive material on a thinned portion of a substrate and sorbing the analyte from the fluid into the sorptive material; and (b) heating the sorptive material in the proximity of the chemiresistor which is located on another substrate or beside the sorptive material on the same substrate and thereby generating a concentrated whiff of the analyte for detection by the chemiresistor.

27. The method of claim 26 wherein the step for sorbing the analyte from the fluid into the sorptive material is performed at a location distal to the chemiresistor.

28. The method of claim 27 further including a step for placing the chemiresistor and sorptive material within a common housing prior to the step for heating the sorptive material.

29. The method of claim 26 wherein the fluid comprises a liquid.

30. The method of claim 26 wherein the fluid comprises a gas or vapor.

31. The method of claim 26 further including steps for measuring a resistance of the chemiresistor immediately prior to the step for heating the sorptive material, and comparing the resistance of the chemiresistor immediately prior to the step for heating the sorptive material with the resistance measured upon heating of the sorptive material, thereby providing a background-corrected measurement of the analyte.

32. The method of claim 26 further including a step for characterizing the analyte by measuring a decay time constant for a change in resistance of the chemiresistor after exposure to the concentrated whiff of the analyte.

33. A chemical-sensing apparatus, comprising:

(a) a chemical preconcentrator having a sorptive material further comprising a polymer or sol-gel host material wherein activated charcoal or a carbon molecular sieve material is embedded, with the sorptive material sorbing a chemical species of interest from a fluid over time and subsequently releasing the chemical species of interest upon heating of the sorptive material; and (b) at least one chemiresistor located proximate to the chemical preconcentrator for sensing the chemical species of interest upon heating of the sorptive material.

* * * * *